United States Patent [19]

Kafrawy

[11] Patent Number: 5,562,944
[45] Date of Patent: Oct. 8, 1996

[54] PROCESS FOR THE PROTECTION OF METALLIC SURFACES

[75] Inventor: Adel Kafrawy, Kingston, Mass.

[73] Assignee: Johnson & Johnson Professional, Inc., Raynham, Mass.

[21] Appl. No.: 520,193

[22] Filed: Aug. 28, 1995

[51] Int. Cl.$^6$ .............. B05D 3/10; B05D 3/12; A61L 27/00
[52] U.S. Cl. .............. 427/156; 427/2.24; 427/2.26
[58] Field of Search .................. 427/2.24, 2.26, 427/156

[56] References Cited

U.S. PATENT DOCUMENTS

| | | | |
|---|---|---|---|
| 3,433,662 | 3/1969 | Webb et al. | 427/156 |
| 3,474,008 | 10/1969 | Buisman | 427/156 |
| 4,086,331 | 4/1978 | Neumann | 424/45 |
| 4,374,063 | 2/1983 | Consolazio et al. | 260/118 |
| 4,430,358 | 2/1984 | Wada | 427/156 |
| 4,468,417 | 8/1984 | Garbutt | 427/156 |
| 5,035,896 | 7/1991 | Apfel et al. | 424/456 |
| 5,199,951 | 4/1993 | Spears | 604/96 |
| 5,270,374 | 12/1993 | Ratliff | 427/156 |
| 5,272,191 | 12/1993 | Ibrahim et al. | 524/35 |
| 5,281,436 | 1/1994 | Swidler | 427/156 |
| 5,411,760 | 5/1995 | Woodhall et al. | 427/421 |
| 5,478,569 | 12/1995 | Berneis et al. | 424/456 |
| 5,482,008 | 1/1996 | Stafford et al. | 119/174 |

*Primary Examiner*—Diana Dudash

[57] ABSTRACT

A method for the protection of porous metallic surfaces, such as titanium tibial tray components, titanium hip stems, and cobalt chrome cup shells of various sizes, during machining, sandblasting, and inspection of orthopaedic implants is disclosed. The process includes the application, cross-linking, and removal of a liquid gelatin coating which provides excellent protection against dirt, dust, lint and other materials from entering the porous surfaces of the prosthetic devices during manufacturing.

4 Claims, No Drawings

5,562,944

PROCESS FOR THE PROTECTION OF METALLIC SURFACES

BACKGROUND OF THE INVENTION

This invention relates to a novel process in which a protective coating is generated on specific areas of porous metallic components of orthopaedic implantable prostheses, such as tibial tray components, hip stems, and acetabular cup shells of various sizes. Many orthopaedic implants have porous surfaces on at least a portion of the prosthesis, with high surface areas, in order to provide a site for bone to grow into the prosthesis which results in a high degree of device stability and fixation to the particular joint site. The manufacture of such porous components is quite complicated due to the need to protect such porous regions from damage or contamination during the multi-step manufacturing processes.

Typical of these manufacturing steps is machining which produces fine metallic particulates, dust, etc. which could be embedded in the valleys of the porous surface. Another step which may be used in the manufacture of the prosthesis is sandblasting. Again, a consequence of this step may include the production of fine debris which could be trapped within the pores of the metallic surface.

For these reasons, the need for a protective coating is essential for the successful production of high quality orthopaedic implants. A suitable coating material has two conflicting requirements. On the one hand, the coating must withstand the harsh effects of the coolant used in the machining step which lasts for at least one hour, as well as the severe force of the sandblasting step, lasting 10 minutes at pressures ranging from 60 to 100 psi. On the other hand, the ideal coating should also be amenable to easy removal using mild and environmentally safe reagents.

Previously, polymethyl methacrylate (PMMA) coatings were applied to the porous surfaces of implantable prosthesis from a 50/50 mixture of acetone/toluene solutions. After application to the porous surface, the solvent mixture was allowed to evaporate, leaving a PMMA layer behind. This process required the use of a fume hood, careful avoidance of spilling of solvents, and avoidance of exposure of these flammable solvents to open flames, sparks or other hazards. PMMA solutions had to be prepared just prior to the coating step, due to the high volatility of the solvents, which could result in changes in PMMA concentration. Another extra cumbersome requirement with the currently used PMMA system is the need to prepare different PMMA solution concentrations for different implants because of the difference in the porous structure of the implant. For example, for hip products a ratio of 30 grams PMMA to 85 ml of solvent is used, whereas in the case of tibial trays, a ratio of 24 grams PMMA to 85 ml solvent is sufficient. Furthermore, for femoral knee components 30 grams PMMA to 100 ml of solvent is used. Each of these preparations require at least 24 hours to ensure complete dissolution of the PMMA in the solvent mixture. These PMMA solutions are usually applied via pneumatic driven syringes where clogging due to premature evaporation of the solvents often occurs. The preparation of the PMMA solution must be conducted in a well ventilated hood and the application of the solution to the prosthetic part is conducted in the hood.

Clearly, the use of a PMMA solution system presents difficulties and a more efficient, environmentally safe, and cost effective approach is desirable.

SUMMARY OF THE INVENTION

The principal object of the present invention is to provide a process for application of a suitable coating for the protection of porous orthopaedic implants which is easy to formulate, easy to apply, strong enough to withstand the harsh conditions of machining and the severe effects of sandblasting, yet amenable toward easy removal after fabrication of the prosthesis using relatively mild, environmentally safe reagents to remove the coating.

In keeping with these objects of the invention, there is provided a process which comprises:

1- The use of a pourable liquid gelatin, completely soluble in water, providing excellent adhesion properties to metals. Such liquid gelatin is a purified gelatin with an average molecular weight of 60,000 daltons. Chemically, it consists of a protein molecule of a complex chain of 20 amino acids. It is amphoteric in nature and its reactivity depends on the pH of the medium in which it is applied.

2- The coating of an orthopaedic implant component with a solution of such liquid gelatin.

3- The immersion of the coated metallic component into a solution of a cross-linking agent.

4- Exposure of the metallic component to machining and sandblasting.

5- Removal of the coating by immersion of the component in an ultrasonic bath containing a mild caustic solution until the coating is dissolved.

DESCRIPTION OF THE INVENTION

The present invention employs a pourable liquid gelatin, completely soluble in water, providing excellent adhesion properties to metals, and at the same time capable of undergoing cross-linking with appropriate cross-linking agents to render the gelatin water insoluble. The preferred liquid gelatin is a purified extract from collagen obtained from cod fish skins. The average molecular weight of the gelatin protein is 60,000 daltons. Chemically, it consists of a protein molecule of a complex chain of 20 amino acids, similar in composition to animal gelatin, except in different proportions. This material has lower amounts of proline and hydroxyproline, but higher amounts of serine, as shown in Table I, where the concentration of these amino acids in liquid gelatin are compared with animal gelatin.

TABLE I

COMPARISON OF AMINO ACID CONTENT
BETWEEN LIQUID GELATIN AND ANIMAL GELATIN

| Amino Acid | Liquid Gelatin (residues/1000 parts) | Calf Skin Gelatin (residues/1000 parts) |
| --- | --- | --- |
| Proline | 106 | 135 |
| Hydroxyproline | 54 | 86 |
| Serine | 65 | 37 |

The low levels of proline and hydroxyproline in liquid gelatin are significant in that they allow the gelatin to remain liquid at room temperature, even at high concentrations. The relatively high levels of serine, a hydroxyl group-containing amino acid, may be responsible for the excellent adhesive properties of the liquid gelatin to the metal surface of the implant. The liquid gelatin is amphoteric in nature and its reactivity depends on the pH of the medium in which it is applied. The liquid gelatin should be capable of being applied to the prosthesis by dipping the prosthesis in the liquid gelatin to completely coat the portion of the prothesis that is dipped. A concentration of about 40 to 50% by weight of the gelatin in water is a useful concentration range, with a preferred concentration of about 45%. The viscosity of the solution is 5,500 to 12,000 centipoise as measured with a Brookfield LV#4 spindle at 30 rpm at 24° C.

Simply applying the liquid gelatin as a coating of the metallic components, would not be effective in withstanding the rigors of the machining and sandblasting steps. The gelatin must be rendered water insoluble and sufficiently strong to act as an effective barrier. The liquid gelatin is cross-linked after it is applied to the surface of the prothesis. The choice of a suitable cross-linking agent and the optimum conditions for effecting such cross-linking are important to the formation of a coating that will protect the surface of the prosthesis. A variety of organic and inorganic cross-linking agents may be used, such as formaldehyde, glutaraldehyde, glyoxal, aluminum sulfate, ferric sulfate, and chromium potassium sulfate referred to as chrome alum. Chrome alum is the most preferred cross-linking agent in providing the required balance of effective protection and ease of removal following the completion of the fabrication stages.

In order to ensure the formation of a coating with homogeneous thickness, total coverage, high resistance to machine coolant and sandblasting operation to which the metallic implant is exposed, cross-linking of the gelatin is required. The preferred cross-linking conditions are immersion of the liquid gelatin coated metallic component in a 5% solution of chrome alum in water for 15 sec at 80° C. The elevated temperature is required to allow the aqueous cross-linking solution to penetrate the interior of the liquid gelatin coating. The high temperature enhances the rate of diffusion of the chrome alum solution into the internal layers of the gelatin coating. At lower rates of diffusion, selective cross-linking is attained only at the surface of the gelatin coating which results in poor resistance toward machining and sandblasting conditions.

A 5% concentration of the cross-linking agent provides sufficient chrome alum molecules to form an adequate number of cross-linking sites to provide a strong gelatin coating capable of withstanding the machining and sandblasting conditions.

The 15 seconds duration for exposure of the gelatin coating to the cross-linking solution is preferred as a suitable compromise between excessive cross-linking which would render the coating peelable during machining and sandblasting on the one hand, and poor cross-linking which would have allowed the gelatin coating to wash away or deform during subsequent fabrication and processing of the implant. Small variations in the concentration, temperature or time will not significantly affect the cross-linking of the gelatin.

When the machining or other processing of the prosthesis is completed, the protective gelatin coating must be removed. The coating of the present invention can be readily removed by immersion of the prosthesis in an ultrasonic bath containing a solution of a strong base, such as sodium hydroxide or potassium hydroxide or mixtures of sodium and potassium hydroxide. A preferred solution is Chem Crest 275 available from Crest Ultrasonic Corporation. This solution is a mixture of sodium and potassium hydroxide and also contains a non-ionic surfactant and tetrasodium ethylene diamine tetra-acetate.

The prosthesis is cleaned by immersion in a solution in an ultrasonic bath at a temperature of between 50° C. and 60° C. Immersion for between 20 and 30 minutes is usually sufficient to completely remove the gelatin from the surface of the prosthesis.

EXAMPLE

Norland HiPure Liquid Gelatin (Norland Products, Inc.), with the following properties was applied to six tibial trays using a syringe with a #20 gauge tapered needle.

Solids concentration - 45% in water

Viscosity @ 75° F. - 6,000 cps

Average molecular weight - 60,000

Gel point - 5°–10° C.

Ash - 0.1%

Preservatives - methyl & propyl p-hydroxybenzoates pH - 5.4

The liquid gelatin was evenly dispensed onto the porous surface starting at the edges. One coat was sufficient in totally covering the beads. The six trays were left to air dry for about 2 hours, then immersed for 15 seconds in a 5% solution of chromium potassium sulfate (chrome alum) at 80° C. to cross-link the gelatin. The coating on each of the trays was completely covering the beads as visually inspected under a microscope at 10×. The six parts were left to dry overnight (24 hrs.) then placed in the bottom of a CNC milling machine where coolant liquid (BLASOCUT 4000 STRONG, Blaser Swisslube, Inc.) was allowed to flow over the parts for 60 minutes. The parts were pat dried with paper towels and then allowed to further air dry for 20 minutes. Visual inspection under the microscope at 10× indicated the presence of a hard coating which provided good coverage of the porous surface. The sandblasting operation was then conducted using a Ray Blast RB-12 Blasting Cabinet (Fortune Metals) for 10 minutes at 60 psi, after which the components appeared to be still protected by the coating as observed at 10× magnification. The six trays were then immersed in an ultrasonic bath (Crest Ultrasonics, Inc.) containing 10% Chem Crest 275° at 125° F. Periodic inspection of the surface of the trays at 10× magnification revealed that at 25 minutes all signs of the liquid gelatin were absent, except for a few spots which were easily removed by slight brushing and a blast from an air gun.

I claim:

1. A method of protecting a surface of an implantable metal prosthesis during the manufacturing process comprising;

a) applying a liquid gelatin to the surfaces of the prosthesis to be protected, b) cross-linking the gelatin to form a hard protective coating on the surfaces c) further mechanically processing the prosthesis, d) contacting the coating with an aqueous solution of a base to remove the protective coating from the prosthesis.

2. The method of claim 1 in which the gelatin is derived from cod fish skins.

3. The process of claim 2 in which the gelatin is cross-linked by contacting the gelatin on the surface of the prosthesis with a solution of chrome alum at a temperature of between 70° and 90° C. for a period of between 10 and 20 seconds.

4. The process of claim 1 in which the base is a mixture of sodium hydroxide and potassium hydroxide.

\* \* \* \* \*